United States Patent [19]

Grohe et al.

[11] Patent Number: 4,859,773
[45] Date of Patent: Aug. 22, 1989

[54] PREPARATION OF 1,8-BRIDGED 4-QUINOLINE-3-CARBOXYLIC ACIDS

[75] Inventors: Klaus Grohe, Odenthal; Michael Schriewer, Leverkusen, both of Fed. Rep. of Germany

[73] Assignee: Bayer Aktiengesellschaft, Leverkusen, Fed. Rep. of Germany

[21] Appl. No.: 172,612

[22] Filed: Mar. 24, 1988

Related U.S. Application Data

[62] Division of Ser. No. 874,182, Jun. 13, 1986, Pat. No. 4,762,831.

[30] Foreign Application Priority Data

Jun. 22, 1985 [DE] Fed. Rep. of Germany ....... 3522406

[51] Int. Cl.⁴ .......................................... C07D 265/34
[52] U.S. Cl. .................................................. 544/101
[58] Field of Search ...................................... 544/101

[56] References Cited

U.S. PATENT DOCUMENTS 4,571,396  2/1986  Hutt et al. ................. 544/101 Y
4,777,253  10/1988 Mitscher et al. ................ 544/101

Primary Examiner—Richard L. Raymond
Attorney, Agent, or Firm—Sprung Horn Kramer & Woods

[57] ABSTRACT

A process for the preparation of a 1,8-bridged 4-quinolone-3-carboxylic acid of the formula

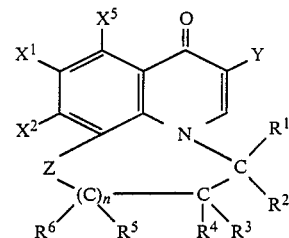

comprising in a first reaction step reacting an enamine of the formula

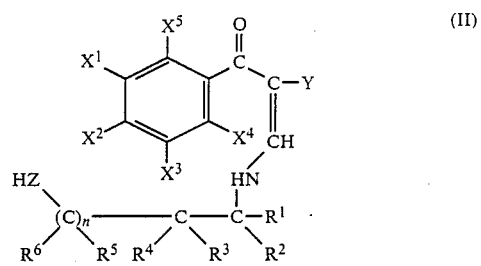

(II)

in an anhydrous, aprotic solvent with one equivalent of a base, at a temperature form 80° C. to 180° C., to give a 4-quinolone-3-carboxylic acid derivative of the formula

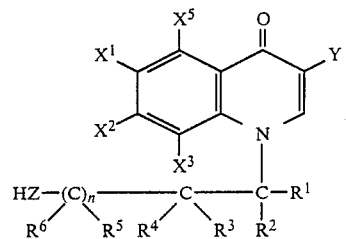

and, in a second reaction step, reacting that with another equivalent of a base, to give the 1,8-bridged 4-quinolone-3-carboxylic acid derivative of the formula (I) and optionally converting the group Y into a carboxyl group or salt thereof. Both steps may be effected simultaneously in a one-pot process without intermediate isolation of the compound II. Some of the compounds are new. The old and new compounds are antibacterials and promote animal growth.

7 Claims, No Drawings

PREPARATION OF 1,8-BRIDGED 4-QUINOLINE-3-CARBOXYLIC ACIDS

This is a division of application Ser. No. 874,182, filed 6/13/86, now U.S. Pat. No. 4,762,831.

The invention relates to a process for the preparation of 1,8-bridged 4-quinolone-3-carboxylic acids, to their intermediates, and to their use as medicaments, in particular as antibacterial agents in human and veterinary medicine.

The preparation of 4-pyridone-3-carboxylic acids by reaction of enamines, which are capable of tautomerism, with o-halogenoarylcarbonyl halides followed by cyclization in the presence of a base is described in European Patent Specification No. 0,004,279.

The invention relates to a process for the preparation of 1,8-bridged 4-quinolone-3-carboxylic acids and to derivatives of the formula (I),

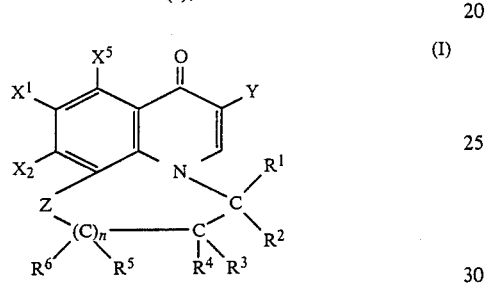

in which
Y represents a carboxyl group, a nitrile group, an ester group —COOR$^7$ or an acid amide group —CONR$^8$R$^9$, R$^7$ representing C$_1$–C$_4$-alkyl, R$^8$ and R$^9$ representing hydrogen or C$_1$–C$_4$-alkyl, and it additionally being possible for R$^9$ to be optionally substituted phenyl, X$^1$ represents hydrogen, nitro, alkyl having 1-3 carbon atoms, or halogen, preferably fluorine, X$^2$ denotes halogen, preferably fluorine or chlorine, alkyl having 1-3 carbon atoms, an alkylsulphonyl group having up to 3 C atoms in the alkyl radical, and a phenylsulphonyl group which is optionally substituted in the aryl radical, X$^5$ can be hydrogen, halogen or methyl, Z represents oxygen, an amino radical NR$^{10}$ R$^{10}$ denoting hydrogen, an alkyl radical having 1-6 carbon atoms which is optionally substituted by halogen, trifluoromethyl, nitro, cyano, hydroxyl, alkoxy or alkylmercapto each having 1-3 carbon atoms, aryloxy, arylthio or an ester radical having 1-3 carbon atoms in the alcohol moiety, or a phenyl radical which is optionally substituted by halogen, a nitro group, an alkyl group having 1-3 carbon atoms, an alkoxy or alkylmercapto group each having 1-3 carbon atoms, and furthermore represents an acyl radical R$^{11}$CO— or R$^{12}$SO$_2$—, R$^{11}$ and R$^{12}$ representing alkyl radicals having 1-6 carbon atoms or optionally substituted phenyl radicals, and can be a

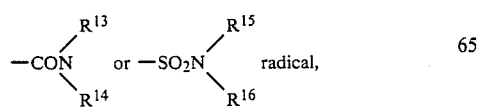

the radicals R$^{13}$ to R$^{16}$ representing hydrogen, alkyl having 1-6 carbon atoms or an optionally substituted phenyl radical, R$^1$, R$^2$, R$^3$, R$^4$, R$^5$ and R$^6$ represent hydrogen, an alkyl group having 1-6 carbon atoms which is optionally substituted once or several times by halogen, in particular chlorine or fluorine, also by nitro, cyano, hydroxyl, alkoxy or alkylmercapto each having 1-3 carbon atoms, aryloxy, arylthio or an ester group having 1-3 carbon atoms in the alcohol moiety, or a phenyl radical, naphthyl radical or heterocyclic radical such as, for example, a thiophene, furan, pyrrole, thiazole, pyridine or pyrimidine radical, each of which is optionally substituted by halogen, nitro, alkyl or akoxy or alkylmercapto each having up to 3 carbon atoms, hydroxyl, aryloxy, arylthio, cyano or an ester radical having 1-3 carbon atoms in the alcohol moiety, and R$^1$ and R$^2$, R$^3$ and R$^4$, R$^5$ and R$^6$ each can form, together with the carbon atom which connects them, a 3-7-membered ring which can optionally be substituted by optionally substituted alkyl radicals having 1-3 carbon atoms or optionally substituted aryl radicals, and furthermore R$^2$ with R$^3$ and/or R$^4$ with R$^5$ each can form, together with the carbon atom to which they are bonded, a 3-7-membered ring which is optionally substituted by optionally substituted alkyl radicals having 1-3 carbon atoms or optionally substituted aryl radicals, and n denotes 0 or 1, and when n denotes 1, R$^5$ and R$^6$ denote halogen, hydroxyl, alkoxy or alkylmercapto each having 1-3 carbon atoms, or a dialkylamino group having 1-3 carbon atoms in the alkyl radicals, characterized in that enamines of the formula (II)

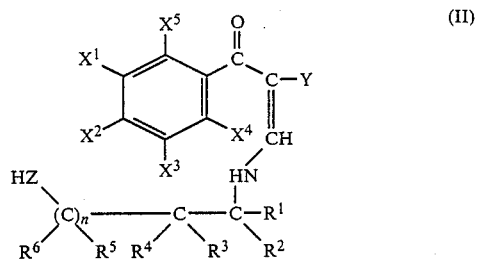

in which
the radicals X$^1$, X$^2$, X$^5$, R$^1$–R$^6$, Z and Y and the symbol n have the abovementioned meaning, and X$^3$ represents halogen, preferably fluorine or chlorine, and the nitro group, and X$^4$ represents halogen, preferably fluorine or chlorine, a nitro group, an alkoxy group having 1-3 carbon atoms in the alkyl moiety, an alkylmercapto or alkylsulphonyl group each having 1-3 carbon atoms in the alkyl radical, and an arylsulphonyl group, are reacted, in a first reaction step, in an anhydrous, aprotic solvent in the presence of one equivalent of a base to give the 4-quinolone-3-carboxylic acid derivatives of the formula (III) (method A).

When, in Method A, the enamino ester (1) is used, and sodium fluoride is used as the base, then the course of the reaction for the first step can be represented by the diagram below:

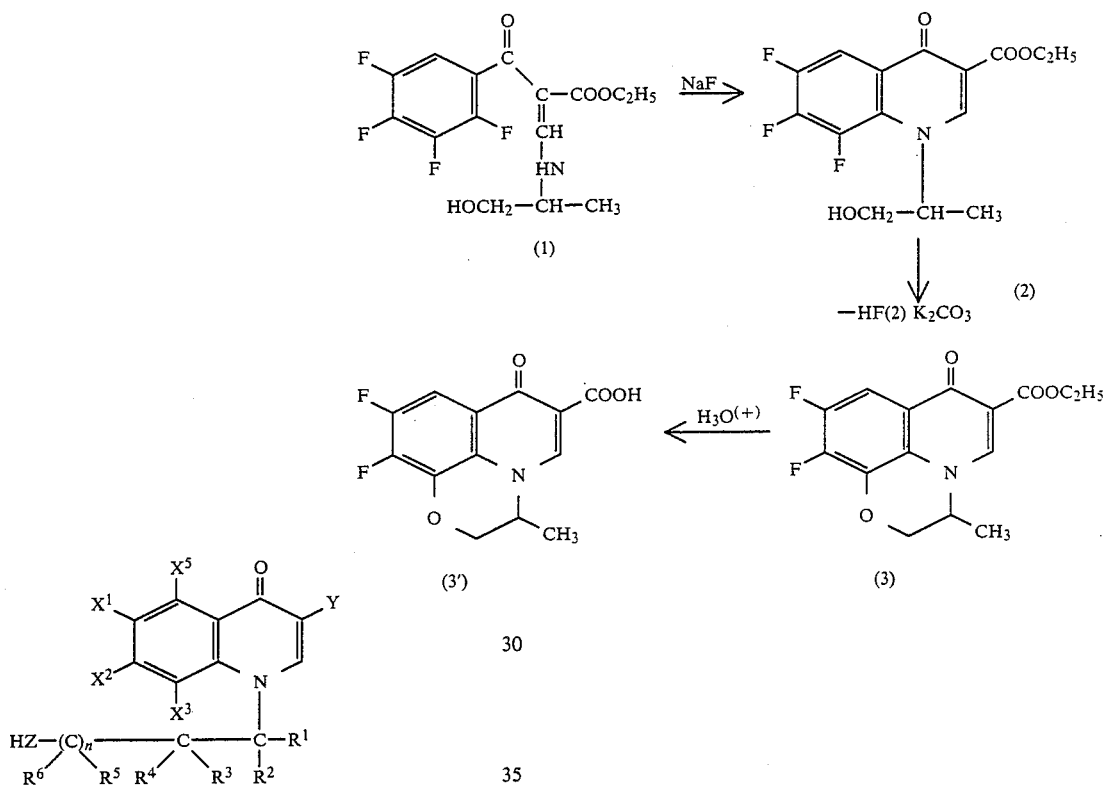

The second cyclization of (2) to (3) is carried out with potassium carbonate.

When, for example, in the reaction by Method B the enamino ester (4) and potassium carbonate are used, then the course of the reaction can be represented by the diagram below:

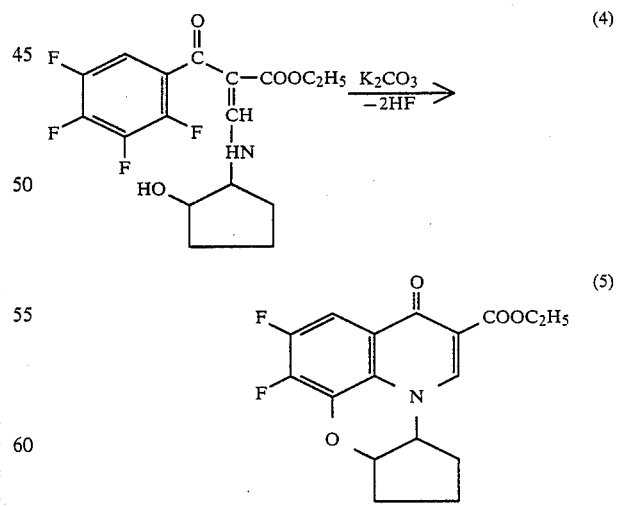

The enamines (II) used as starting materials in Methods A and B can be prepared by reaction of the corresponding enol ethers (IV) with the primary amines (V), $X^1$–$X^5$, $R^1$–$R^6$, Z, Y and n having the abovementioned meaning.

(III)

in which
the radicals $X^1$, $X^2$, $X^3$, $X^5$, $R^1$ $R^6$, Z and
Y and the symbol n have the abovementioned meanings, and, in a second reaction step, the second cyclization to give the 1,8-bridged 4-quinolone-3-carboxylic acid derivatives of the abovementioned formula (I) is carried out in the presence of another equivalent oof a base, and, where appropriate, the group Y is converted in a manner known per se into the carboxyl group, and, where appropriate, this is converted into its salts.

The term "substituted aryl" represents substituted phenyl and substituted naphthyl, preferably substituted phenyl.

The term "substituted phenyl" represents a phenyl radical with up to three substituents. The substituents include alkyl with 1–3 carbon atoms, preferably methyl; halogen, preferably chlorine and fluorine; alkoxy with 1–3 carbon atoms, preferably methoxy; alkylmercapto with 1–3 carbon atoms, preferably methylmercapto; nitro, cyano and ester groups with up to 3 carbon atoms in the alcohol part.

It is particularly advantageous to react the enamines (II) with 2 equivalents of a base, without intermediate isolation of (III), in a so-called one-pot reaction to give the 1,8-bridged 4-quinolone-3-carboxylic acid derivatives (I) (method B).

It is extremely surprising that the 1,8-bridging in the second reaction step of the process according to the invention takes place with the involvement of a leaving group $X^3$ which is not activated mesomerically by the carbonyl group being in the meta position.

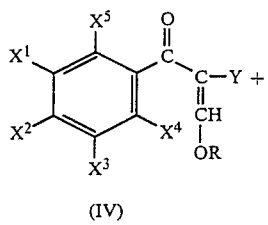

(IV)

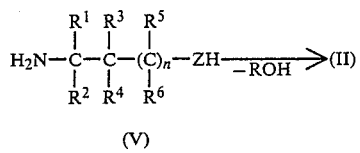

(V)

The enol ethers (IV) are known or can be prepared in accordance with the following general scheme of reaction:

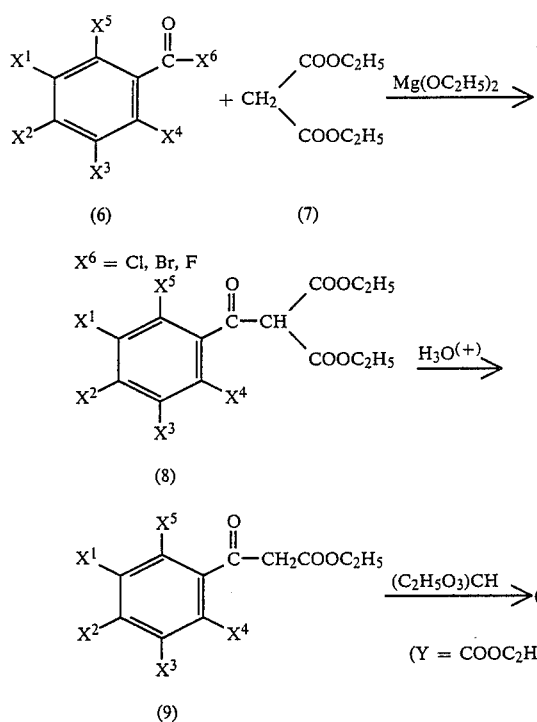

According to this, diethyl malonate (7) is acylated, in the presence of magnesium ethylate, with the appropriate benzoyl halide (6) to give the acylmalonic ester (8) (Organicum, 3rd edition 1964, page 438).

By partial hydrolysis and decarboxylation of (8) in aqueous medium with catalytic amounts of sulphuric acid or 4-toluenesulphonic acid, a good yield of the ethyl benzoylacetate (9) is obtained, and this is converted into the ethyl 2-benzoyl-3-ethoxyacrylate (IV, R=$C_2H_5$) with triethyl orthoformate/acetic anhydride. The reaction of (IV) with the amines (V) in a solvent such as, for example, methylene chloride, in an alcohol, chloroform, cyclohexane or toluene, leads to the desired intermediates (II) in a slightly exothermic reaction.

The cyclization reactions (II)→(III), (III)→(I) and (II)→(I) are carried out in a temperature range of about 60°–300° C., preferably 80°–180° C.

Diluents which can be used are dioxane, dimethyl sulphoxide, n-methylpyrrolidone, sulpholane, hexamethylphosphoric trisamide and, preferably, N,N-dimethylformamide.

The cyclocondensations can be carried out under atmospheric pressure as well as under elevated pressure. In general, they are carried out under pressures between about 1 and about 100 bar, preferably 1 and 10 bar.

Suitable acid-binding agents for the cyclization reactions (II)→(III), (III)→(I) and (II)→(I) are potassium tert.-butanolate, 1,4-diazabicyclo[2,2,2]octane (DABCO), 1,8-diazabicyclo[5,4,0]undec-7-ene (DBU), butyllithium, lithiumphenyl, phenyl magnesium bromide, sodium methylate, sodium ethylate, sodium hydride, and sodium or potassium carbonate. Potassium or sodium fluoride are particularly preferred when hydrogen fluoride is to be eliminated.

In general, one equivalent of base is used for both the primary cyclization (II)→(III) and the second cyclization (III)→(I). If the two cyclization reactions are combined in a "one-pot reaction" (II)→(I), then 2 equivalents of the abovementioned bases must be used. It may be advantageous to use an excess of 10 mol-% of base in the cyclocondensations (III)→(I) and (II)→(I).

The hydrolysis of the esters, nitriles and amides (I) which takes place in the final step to give the corresponding carboxylic acids can be carried out under the customary and known acid or basic conditions.

2,3,4,5-Tetrafluorobenzoyl chloride and pentafluorobenzoyl chloride used as starting materials for this synthetic route are known. 3,5-dichloro-2,4-difluorobenzoyl fluoride (boiling point 97°/20 mbar; $n_D^{20}=1.5148$) and 5-chloro-2,3,4trifluorobenzoyl fluoride (boiling point 66°–70°/20 mbar; $n_D^{20}=1.4764$) are obtained together when tetrachlorobenzoyl chloride is heated with potassium fluoride in sulpholane at elevated temperatures:

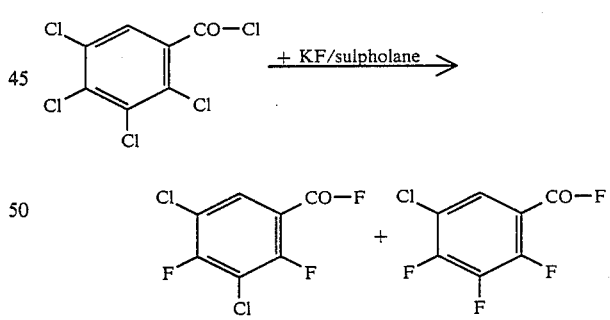

The chlorination of 2,4,5-trifluorobenzoic acid in chlorosulphonic acid leads to 3-chloro-2,4,5-trifluorobenzoic acid which is reacted, as the crude product, with thionyl chloride to give 3-chloro-2,4,5-trifluorobenzoyl chloride (boiling point: 94°/18 mbar; $n_D^{20}=1.5164$):

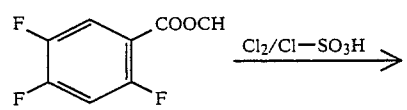

-continued

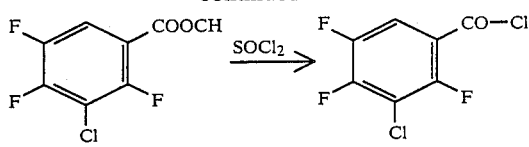

2,4-Dichloro-5-fluoro-3-nitrobenzoyl chloride is obtained by nitration of the known 2,4-dichloro-5-fluorobenzoic acid to give 2,4-dichloro-5-fluoro-3-nitrobenzoic acid, and reaction of the latter with thionyl chloride.

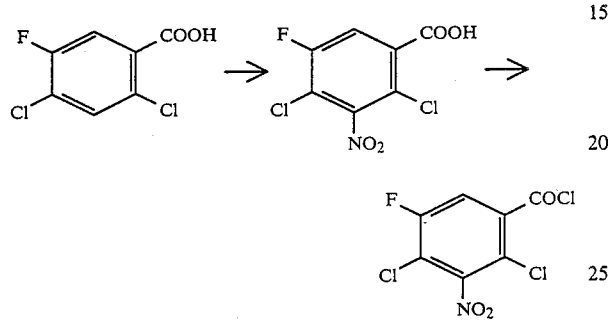

The amines of the formula (V) used as starting materials are known. Examples which may be mentioned are: 2-aminoethanol, 2-aminopropanol, 3-aminopropanol, 2-amino-2-methylpropanol, 2-aminocyclopentanol, 2-aminocyclohexanol, 2-(2-aminoethylamino)-ethanol, 2-amino-2-phenylethanol, ethylenediamine, 2-aminobutanol, 1,3-diaminopropane, 1-amino-2,3-propanediol, 2-amino-3-phenylpropanol, 2-amino-1-phenyl-1,3-propanediol, N-phenylethylenediamine, N-benzylethylenediamine and 2-aminomethylcyclohexanol.

The invention also relates to 1,8-bridged 4-quinolone-3-carboxylic acid derivatives of the formula (I')

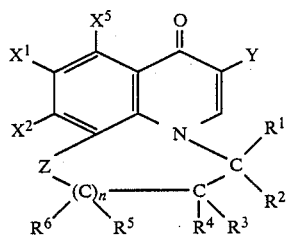

in which $X^1$, $X^2$, $X^5$, $R^1$ to $R^6$, Z and Y and n have the abovementioned meaning, with the proviso that $X^1$ and $X^2$ cannot both represent fluorine when n=0 and $R^1$ and $R^4$ represent hydrogen and $R^2$ and $R^3$ represent hydrogen or lower alkyl.

The invention likewise relates to the compounds of the formulae (II) and (III).

The 1,8-bridged 4-quinolone-3-carboxylic acids, according to the invention, of the formulae (I) and (I') and their derivatives have antibacterial activity. They can also be used as intermediates for the synthesis of highly active bactericides. Thus, the bactericide Ofloxacin is obtained by reaction of the pyridobenzoxazincarboxylic acid (3') with 1-methylpiperazine.

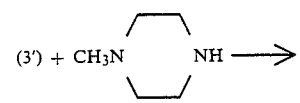

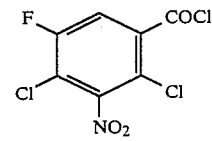

Ofloxacin

The examples which follow illustrate the invention:

PREPARATION OF THE STARTING COMPOUNDS

Example A

Ethyl 2-(2,4-dichloro-5-fluoro-3-nitrobenzoyl)-3-ethoxyacrylate (a) 2,4-dichloro-5-fluoro-3-nitrobenzoic acid 40 ml of concentrated nitric acid are added dropwise to 34 ml of concentrated sulphuric acid, while cooling in ice and stirring. 20.9 g of 2,4-dichloro-5-fluorobenzoic acid are introduced in portions into this nitration mixture, during which the temperature rises to 45°–50° C. The mixture is then heated at 90°–100° C. for 3 hours, cooled to room temperature, and poured onto 350 ml of ice-water, and the precipitate is filtered off with suction and washed with water. The moist crude product was dissolved in 30 ml of hot methanol, and 150 ml of $H_2O$ are added to the solution. The precipitate is cooled, filtered off with suction, washed with $CH_3OH/H_2O$ and dried in vacuo at 80° C. 21.2 g of crude 2,4-dichloro-5-fluoro-3-nitrobenzoic acid are obtained. It is sufficiently pure for the subsequent reactions. A sample recrystallized from toluene/petroleum ether provides crystals of melting point 192° C.

(b) 2,4-Dichloro-5-fluoro-3-nitrobenzoyl chloride 106.6 g of 2,4-dichloro-5-fluoro-3-nitrobenzoic acid are heated to boiling under reflux with 250 ml of thionyl chloride for 2 hours. The excess thionyl chloride is then removed by distillation under atmospheric pressure, and the residue is fractionated under high vacuum. 104.7 g of 2,4-dichloro-5-fluoro-3-nitrobenzoylchloride distil over at 110°–115° C./0.08–0.09 mbar. Crystals of melting point 35°–37° C. form on standing.

(c) Ethyl 2,4-dichloro-5-fluoro-3-nitrobenzoyl)acetate

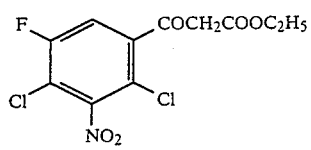

2.1 g of tetrachloromethane are added to 10.1 g of magnesium turnings in 21 ml of ethanol and, after evolution of hydrogen has started, a mixture of 66.6 g of diethyl malonate, 40 ml of ethanol and 150 ml of toluene is added dropwise at 50°-60° C. The mixture is stirred at this temperature for 1 hour, then cooled to −5 to −10° C., and a solution of 109.2 g of 2,4-dichloro-5-fluoro-3-nitrobenzoyl chloride in 50 ml of toluene is slowly added dropwise. The mixture is then stirred at 0° C. for 1 hour, brought to room temperature overnight, and then heated at 40°-50° C. for 2 hours. The reaction mixture is cooled in ice, and a mixture of 160 ml of water and 10.4 ml of concentrated sulphuric acid is added, and the organic phase is separated off. The aqueous phase is extracted with toluene, and the combined organic extract is washed with saturated sodium chloride solution, dried with sodium sulphate, and the solvent is removed in vacuo. 144.5 g of diethyl (2,4-dichloro-5-fluoro-3-nitrobenzoyl)malonate are obtained as a crude product. 200 ml of water and 0.6 g of 4-toluenesulphonic acid are added to this, and the mixture is heated under reflux for 3 hours, extracted with methylene chloride, and the extract is dried with Sodium sulphate and the solvent is removed by distillation in vacuo. 118 g of substituted benzoyl acetic ester are obtained as a crude product. It is sufficiently pure for the subsequent reactions.

(d) Ethyl 2-(2,4-dichloro-5-fluoro-3-nitrobenzoyl)-3-ethoxyacrylate

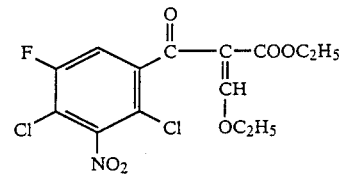

244.8 g of ethyl(2,4-dichloro-5-fluoro-3-nitrobenzoyl)acetate are heated with 166 g of triethyl orthoformate and 185 g of acetic anhydride at 150°-160° C. for 3 hours. The mixture is then concentrated in vacuo, and 270 g of ethyl benzoylethoxyacrylate are obtained as an oily residue.

EXAMPLE 1

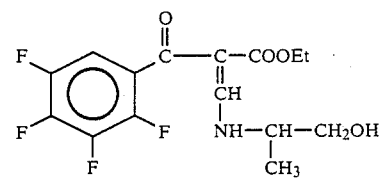

8 g of ethyl 3-ethoxy-2-(2,3,4,5-tetrafluorobenzoyl)acrylate (Le A 22 802) are initially introduced into 10 ml of ethanol. While cooling in ice, a solution of 2.06 g of DL-2-amino-1-propanol in 10 ml of ethanol is added dropwise. The mixture is allowed to warm to room temperature and is stirred for 2 hours. It is then concentrated in vacuo. 9.1 g of ethyl 2-(2,3,4,5-tetrafluorobenzoyl)-3-(1-hydroxy-2-propylamino)acrylate remain behind as a crude oil.

The following aminoacrylic esters are obtained in analogy to Example 1 (Table 1).

TABLE 1

Aminoacrylic esters of the formula (II)
$n = 0$, $Z = 0$ (oxygen)

| Example | $X^1$ | $X^2$ | $X^3$ | $X^4$ | $X^5$ | $R^1$ | $R^2$ | $R^3$ | $R^4$ | $\gamma$ | Melting point |
|---|---|---|---|---|---|---|---|---|---|---|---|
| 2* | F | Cl | $NO_2$ | Cl | H | H | H | H | H | COOEt | oil |
| 3* | F | F | F | H | H | H | H | H | H | " | oil |
| 4* | F | Cl | $NO_2$ | Cl | H | Me | H | H | H | " | oil |
| 5 | F | F | F | F | H | H | H | Me | H | " | oil |
| 6* | F | Cl | $NO_2$ | Cl | H | H | H | Me | H | " | oil |
| 7 | F | F | F | F | H | Me | Me | H | H | " | 93-94° |
| 8* | F | Cl | $NO_2$ | Cl | H | Me | Me | H | H | " | 78-80° |
| 9 | F | F | F | F | H | Me | Me | Me | H | " | oil |
| 10 | F | F | F | F | H | —(CH$_2$)$_5$— | | H | H | " | oil |
| 11 | F | F | F | F | H | H | H | Ph | H | " | *117-19° |
| 12* | F | Cl | $NO_2$ | Cl | H | H | H | Ph | H | " | 148-50° |
| 13 | F | F | F | F | H | iPr | H | H | H | " | oil |
| 14 | F | F | F | F | H | $CH_2OH$ | H | H | H | " | oil |
| 15 | F | F | F | F | H | H | H | $CH_2OH$ | H | " | oil |
| 16 | F | F | F | F | H | H | H | $CH_2F$ | H | " | oil |
| 17 | F | F | F | F | H | Et | H | H | H | " | oil |
| 18 | F | F | F | F | H | H | —(CH$_2$)$_3$— | | H | " | oil |
| 19 | F | F | F | F | H | H | —(CH$_2$)$_4$— | | H | " | oil |
| 20** | F | Me | $NO_2$ | Cl | H | H | H | H | H | " | oil |

| Example | $X^1$ | $X^2$ | $X^3$ | $X^4$ | $X^5$ | $R^1$ | $R^2$ | $R^3$ | $R^4$ | $R^5$ | $R^6$ | $\gamma$ | Melting point |
|---|---|---|---|---|---|---|---|---|---|---|---|---|---|
| 21 | F | F | F | F | H | H | H | H | H | H | H | COOEt | 77-79° |
| 22 | F | F | F | F | H | H | —(CH$_2$)$_4$— | | H | H | H | " | oil |
| 23* | F | Cl | $NO_2$ | Cl | H | H | H | H | H | H | H | " | oil |

*In this case the 2-(2,4-dichloro-5-fluoro-3-nitrobenzoyl)-3-ethoxyacrylic acid ethyl ester (Example A) is used
**In this case the ethyl 2-(2-chloro-5-fluoro-4-methyl-3-nitrobenzoyl)-3-ethoxy-acrylate (See U.S. Ser. No. 795,056, filed November 5, 1985, now pending, corresponding to German Published Specification 3,441,788) is used.

STEPWISE CYCLIZATION OF AMINOACRYLIC ESTERS (METHOD A)

Example 24

(a)

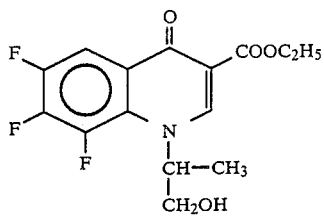

9 g of product from Example 1 are heated with 3.2 g of NaF in 66 ml of DMSO at 140° C. for 4 hours. After the mixture has been cooled to room temperature, it is diluted with water and the precipitate is isolated. Yield: 7.6 g of ethyl 6,7,8-trifluoro-1,4-dihydro-1-(1-hydroxy-2-propyl)-4-oxo-3-quinolinecarboxylate. Melting point: 155°–57° C.

(b)

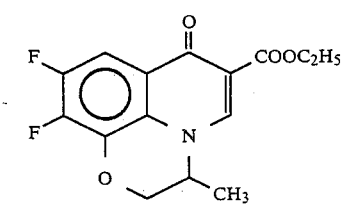

7.6 g of the compound from (a) are heated with 38 g of potassium carbonate in 34 ml of DMF at 140°–45° C. for 2 hours. After the mixture has been cooled to room temperature and diluted with water, the resulting solid is isolated. Yield 4.8 g of ethyl 9,10-difluoro-2,3-dihydro-3-methyl-7-oxo-7H-pyrido[1,2,3-de] [1,4]benzoxazine-6-carboxylate. Melting point 240°–2° C.

ONE STEP CYCLIZATION (METHOD B)

Example 25

8 g of the product from Example 18 are heated in 40 ml of DMF with 3.3 g of potassium carbonate at 140°–45° C. for 4 hours. After the mixture has been cooled to room temperature, it is diluted with water and cooled. The resulting precipitate is separated off and, if necessary, recrystallized from glycol monomethyl ether. Yield: 5.4 g of ethyl 5,6-difluoro-3a,11a-dihydro-8-oxo-8H-cyclopenta [1,2-b]pyrido[1,2,3-de] [1,4]benzoxazine-9-carboxylate. Melting point: 255°–58°.

The following quinolone carboxylic esters are obtained in analogy to Example 25 (Table 2):

TABLE 2

Quinolonecarboxylic esters of the formula (I) n = 0, Z = 0 (oxygen)

| Example | $X^1$ | $X^2$ | $X^5$ | $R^1$ | $R^2$ | $R^3$ | $R^4$ | $R^5$ | $R^6$ | γ | Melting point |
|---|---|---|---|---|---|---|---|---|---|---|---|
| 26 | F | Cl | H | H | H | H | H | | | COOEt | 225–60° |
| 27 | F | F | H | H | H | H | H | | | COOEt | 229–32° |
| 28 | F | Cl | H | Me | H | H | H | | | COOEt | 250° |
| 29 | F | F | H | H | H | Me | H | | | COOEt | 248–50° |
| 30 | F | Cl | H | H | H | Me | H | | | COOEt | 256–8° |
| 31 | F | F | H | Me | Me | H | H | | | COOEt | 288–90° |
| 32 | F | F | H | Me | H | Me | H | | | COOEt | 186–9° |
| 33 | F | F | H | —(CH$_2$)$_5$— | | H | H | | | COOEt | 234–40° |
| 34 | F | F | H | H | H | Ph | H | | | COOEt | 274–6° |
| 35 | F | Cl | H | H | H | Ph | H | | | COOEt | 280–2° |
| 36 | F | F | H | iPr | H | H | H | | | COOEt | 105–10° |
| 37 | F | F | H | CH$_2$OH | H | H | H | | | COOEt | 253–55° |
| 38 | F | F | H | H | H | CH$_2$OH | H | | | COOEt | 228–30° |
| 39 | F | F | H | H | H | CH$_2$F | H | | | COOEt | 226–8° |
| 40 | F | F | H | Et | H | H | H | | | COOEt | 226–8° |
| 41 | F | F | H | H | —(CH$_2$)$_4$— | | H | | | COOEt | 278–9° |
| 42 | F | Me | H | H | H | H | H | | | COOEt | >300° |
| 43 | F | F | H | H | H | H | H | H | H | COOEt | 212–15° |
| 44 | F | F | H | H | —(CH$_2$)$_4$— | | H | H | H | COOEt | 178–82° |
| 45 | F | Cl | H | H | H | H | H | H | H | COOEt | 142–4° |

EXAMPLE 46

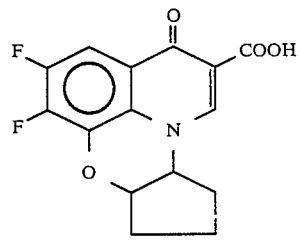

5.4 g of the product from Example 25 are heated in a mixture of 17 ml of acetic acid, 16 ml of water and 1.6 ml of concentrated sulphuric acid at 140° C. (bath) for 4 hours. The mixture is then cooled, diluted with water, and the solid is isolated. Yield: 4.4 g Melting point: 270° (decomposition)

The following quinolonecarboxylic acids are obtained in analogy to Example 46 (Table 3):

TABLE 3

Quinolonecarboxylic acids of the formula (I) n = 0, Z = 0 (oxygen)

| Example | $X^1$ | $X^2$ | $X^5$ | $R^1$ | $R^2$ | $R^3$ | $R^4$ | $R^5$ | $R^6$ | $\gamma$ | Melting point |
|---|---|---|---|---|---|---|---|---|---|---|---|
| 47 | F | F | H | H | H | H | H | | | COOH | 270–3° |
| 48 | F | F | H | Me | H | H | H | | | COOH | >300° |
| 49 | F | F | H | H | H | Me | H | | | COOH | 288–90° |
| 50 | F | Cl | H | H | H | Me | H | | | COOH | 299–300° |
| 51 | F | F | H | Me | Me | H | H | | | COOH | >300° |
| 52 | F | F | H | Me | H | Me | H | | | COOH | 268–70° |
| 53 | F | F | H | —(CH$_2$)$_5$— | | H | H | | | COOH | >300° |
| 54 | F | Cl | H | H | H | Ph | H | | | COOH | >300° d) |
| 55 | F | F | H | H | H | Ph | H | | | COOH | 300° |
| 56 | F | F | H | iPr | H | H | H | | | COOH | 290–94° |
| 57 | F | F | H | CH$_2$OH | H | H | H | | | COOH | 244–46° |
| 58 | F | F | H | H | H | CH$_2$OH | H | | | COOH | 148–50° |
| 59 | F | F | H | Et | H | H | H | | | COOH | 292–4° |
| 60 | F | F | H | H | —(CH$_2$)$_4$— | | H | | | COOH | 294–6° |
| 61 | F | Me | H | H | H | H | H | | | COOH | >300° (d) |
| 62 | F | F | H | H | H | H | H | H | H | COOH | 230–3° |
| 63 | F | F | H | H | —(CH$_2$)$_4$— | | H | H | H | COOH | 274–6° (d) |
| 64 | F | Cl | H | H | H | H | H | H | H | COOH | 270° |

EXAMPLE 65

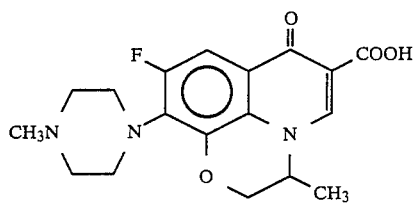

26 g of the product from Example 48 and 28.7 g of N-methylpiperazine are heated in 290 ml of DMSO at 140° C. for 2½ hours. Then all the volatile constituents are removed by distillation under high vacuum. The residue is boiled with ethanol. The mixture is allowed to cool, and the solid is separated off.

Yield: 23 g of 9-fluoro-2,3-dihydro-3-methyl-10-(1-methylpiperazinyl)-7-oxo-7H-pyrido[1,2,3-de] [1,4]-benzoxazine-6-carboxylic acid (ofloxacin). Melting point: 278°–80° (decomposition).

EXAMPLE 66

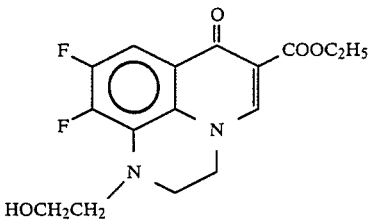

6.4 g of ethyl 3-ethoxy-2-(2,3,4,5-tetrafluorobenzoyl) acrylate are initially introduced into 8 ml of ethanol. Now, while cooling in ice, 2.3 g of 2-(2-aminoethylamino)ethanol dissolved in 15 ml of ethanol are added dropwise. The mixture is allowed to reach room temperature and is stirred for two hours. It is then evaporated in vacuo. The oily residue consists of 8.6 g of crude aminoacrylic ester. 8.4 g of the crude aminoacrylic ester are heated with 3.3 g of potassium carbonate in 40 ml of DMF at 140° C. for 4 hours. After the mixture has been cooled to room temperature, it is diluted with water, and the precipitate is isolated. The yield, after drying in vacuo over KOH, is 3.1 g of ethyl 9,10-difluoro-2,3-dihydro-1-(2-hydroxyethyl)-7-oxo-7H-pyrido[1,2,3-de]quinoxaline-6-carboxylate. Melting point: 244°–5°.

The compounds according to the invention exhibit a broad antibacterial spectrum against Gram-positive and Gram-negative germs, in particular against Enterobacteriaceae; above all against those which are resistant towards various antibiotics, such as, for example, penicillins, cephalosporins, aminoglycosides, sulphonamides or tetracyclines, coupled with a low toxicity.

These useful properties enable them to be used as chemotherapeutic active compounds in medicine and as substances for preserving inorganic and organic materials, in particular all types of organic materials, for example polymers, lubricants, paints, fibres, leathers, paper and wood, and foodstuffs and water.

The compounds according to the invention are active against a very broad spectrum of microorganisms. Gram-positive and Gram-negative bacteria and bacteria-like microorganisms can be combated and the diseases caused by these pathogens can be prevented, alleviated and/or cured with their aid.

The compounds according to the invention are particularly active against bacteria and bacteria-like microorganisms. They are therefore particularly suitable in human medicine and veterinary medicine for the prophylaxis and chemotherapy of local and systemic infections caused by these pathogens.

For example, local and/or systemic diseases caused by the following pathogens or by mixtures of the following pathogens can be treated and/or prevented: Gram-positive Cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative Cocci (*Neisseria gonorrhoeae*) and Gram-negative rod-shaped bacillae, such as Enterobacteriaceae, for example *Escherichia coli, Haemophilus influenzae,* Citrobacter (*Citrob. freundii* and *Citrob. divernis*), Salmonella and Shigella; and furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the genus Acinetobacter. The antibacterial spectrum moreover includes the genus Pseudomonas (*Ps. aeruginosa* and *Ps. maltophilia*) and strictly anaerobic bacteria, such as, for example, *Bacteroides fragilis*, representatives of the genus Peptococcus, Peptostreptococcus and the genus Clostridium; and furthermore mycoplasms (*M. pneumoniae, M. hominis* and *M. urealyticum*) and mycobacteria, for example *Mycobacterium tuberculosis*.

The above list of pathogens is merely representative and is by no means to be considered limiting. The following may be mentioned as examples of diseases which are caused by the stated pathogens or mixed infections and may be prevented, alleviated or cured by the compounds according to the invention:

Infectious diseases in humans, such as for example otitis, pharyngitis, pneumonia, peritonitis, pyelonephritis, cystitis, endocarditis, systemic infections, bronchitis (acute, chronic), septic infections, diseases of the upper respiratory tract, diffuse panbronchiolitis, pulmonary emphysema, dysentery, enteritis, hepatic abscesses, urethritis, prostatitis, epididymitis, gastrointestinal infections, infections of the bones and joints, cystic fibroses, skin infections, postoperative wound infections, abscesses, phlegmone, wound infections, infected burns, burn wounds, infections in the mouth area, infections after tooth operations, osteomyelitis, septic arthritis, cholecystitis, peritonitis with appendicites, cholangitis, intraabdominal abscesses, pancreatitis, sinusitis, mastoidites, mastitis, tonsillitis, typhoid, meningitis and infections of the nervous system, salpingitis, endometritis, genital infections, pelvic peritonitis and eye infections.

Bacterial infections in other species in addition to humans can also be treated. The following may be mentioned as examples:

pigs: Coli-diarrhea, enterotoxemia, sepsis, dysentery, salmonellosis, metritis-mastitis-agalactiae-syndrome, mastitis;

ruminants (cattle, sheep, goats): diarrhea, sepsis, bronchopneumonia, salmonellosis, pasteurellosis;

horses: bronchopneumonias, septic arthritis, puerperal and postpuerperal infections, salmonellosis;

dogs and cats: bronchopneumonia, diarrhea, dermatitis, otitis, urinary tract infections, prostatitis;

poultry (hens, turkerys, quails, pigeons, ornamental birds and others): mycoplasmosis, *E. coli* infections, chronic diseases of the respiratory tract, salmonellosis, pasteurellosis, psittacosis.

It is also possible to treat bacterial diseases which occur during the breeding and care of useful and ornamental fish, the antibacterial spectrum extending beyond the above mentioned pathogens to include further pathogens, for example Pasteurella, Brucella, Campylobacter, Listeria, Erysipelothrix, Corynebacteria, Borella, Treponema, Nocardia, Rickettsia and Yersinia.

The present invention includes pharmaceutical formulations which, in addition to non-toxic, inert pharmaceutically suitable excipients, contain one or more compounds according to the invention or consist of one or more active compounds according to the invention, and to processes for the preparation of these formulations.

The present invention also includes pharmaceutical formulations in dosage units. This means that the formulation are present in the form of individual parts, for example tablets, dragees, capsules, pills, suppositories and ampoules, the active compound content of which correspond to a fraction or a multiple of an individual dose. The dosage units can contain, for example, 1, 2, 3 or 4 individual doses or $\frac{1}{2}$, $\frac{1}{3}$ or $\frac{1}{4}$ of an individual dose.

An individual dose preferably contains the amount of active compound which is given in one administration and which usually corresponds to a whole, one half, one third or one quarter of a daily dose.

By non-toxic, inert pharmaceutically suitable excipients there are to be understood solid, semi-solid or liquid diluents, fillers and formulation auxiliaries of all types.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can also be provided with the customary coatings and shells, optionally containing opacifying agents, and can also be of such composition that they release the active compound or compounds only, or preferentially, in a particular part of the intestinal tract, if appropriate in a delayed manner, examples of embedding compositions which can be used being polymeric substances and waxes.

The active compound or compounds, if appropriate with one or more of the abovementioned excipients, can also be in microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams, and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Powders and sprays can contain, in addition to the active compound or compounds, the customary excipients, for example lactose, talc, silicic acid, aluminium hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, suspending agents, for example ethoxylated isostearyl alcohols, polyoxyethylene sorbitol and Sorbitan esters, microcrystalline cellulose, aluminium metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds in addition to the compounds according to the invention.

The abovementioned pharmaceutical formulations are prepared in the customary manner by known methods, for example by mixing the active compound or compounds with the excipient or excipients.

The preparations mentioned can be used in humans and animals either orally, rectally, parenterally (intravenously, intramuscularly, subcutaneously), intracisternally, intravaginally, intraperitoneally, locally (powder, ointment, drops) and for the treatment of infections in antra and body cavities. Possible preparations which are suitable are injection solutions, solutions and suspensions for oral treatment, gels, pour-on formulations, emulsions, ointments or drops. Ophthalmological and dermatological formulations, silver and other salts, ear drops, eye ointments, powders or solutions can be used for local treatment. Animals can also ingest the preparations in suitable formulations via their feed or drinking water. Furthermore gels, powders, dusting powders, tablets, delayed-action tablets, premixes, concentrates, granules, pellets, tablets, boli, capsules, aerosols, sprays and inhalants can be used in humans and animals. In addition the compounds according to the invention can be incorporated into other excipients such as for example plastics, (plastic chains for local treatment), collagen or bone cement.

In general, it has proved advantageous both in human medicine and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably contains the active compound or compounds according to the invention in amounts of about 1 to 80, in particular 3 to 30 mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place.

Thus it can in some cases be sufficient to manage with less than the abovementioned amount of active compound, whilst in other cases the abovementioned amount of active compound must be exceeded. The particular optimum dosage required and the mode of administration of the active compound can easily be determined by any expert on the basis of his expert knowledge.

The new compounds can be administered in the customary concentrations and formulations together with the feed or with feed formulations or with the drinking water. Infection by Gram-negative or Gram-positive bacteria can thereby be prevented, alleviated and/or cured and promotion of growth and improvement in the feed utilization can thereby be achieved.

The following table shows the MIC values of some of the compounds according to the invention compared with Ciprofloxacine.

| | MIC (mcg/ml) | |
|---|---|---|
| Strain | Example No. 61 | Example No. 64 |
| *E. coli* Neumann | 0.125 | 0.5 |
| *E. coli* T 7 | 0.5 | 1 |
| *E. coli* A 261 | 0.5 | 1 |
| Klebsiella 8085 | 0.125 | 0.25 |

Agar dilution test (Isosensitest medium)
Denley multipoint inoculator

It will be understood that the specification and examples are illustrative but not limitative of the present invention and that other embodiments within the spirit and scope of the invention will suggest themselves to those skilled in the art.

We claim:

1. A process for the preparation of a 1,8-bridged 4-quinolone-3-carboxylic acid of the formula

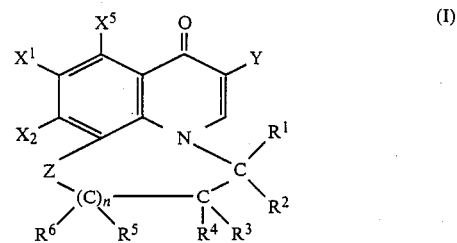

in which
Y represents a carboxyl group, a nitrile group, an ester group —COOR$^7$ or an acid amide group —CONR$^8$R$^9$, R$^7$ representing C$_1$–C$_4$-alkyl,
R$^8$ and R$^9$ representing hydrogen or C$_1$–C$_4$-alkyl, and it additionally being possible for R$^9$ to be optionally substituted phenyl,
X$^1$ represents hydrogen, nitro, alkyl having 1-3 carbon atoms, or halogen,
X$^2$ denotes halogen, alkyl having 1-3 carbon atoms, an alkylsulphonyl group having up to 3 C atoms in the alkyl radical, and a phenylsulphonyl group which is optionally substituted in the aryl radical,
X$^5$ is hydrogen, halogen or methyl,
Z represents oxygen, an amino radical NR$^{10}$,
R$^{10}$ denoting hydrogen, an alkyl radical having 1-6 carbon atoms which is optionally substituted by halogen, trifluoromethyl, nitro, cyano, hydroxyl, alkoxy or alkylmercapto each having 1-3 carbon atoms, aryloxy, arylthio or ester radical having 1-3 carbon atoms in the alcohol moiety, or a phenyl radical which is optionally substituted by halogen, a nitro group, an alkyl group having 1-3 carbon atoms, an akoxy or alkylmercapto group each having 1-3 carbon atoms, or furthermore represents an acyl radical $R^{11}CO-$ or $R^{12}SO_2-$, $R^{11}$ and $R^{12}$ representing alkyl radicals having 1-6 carbon atoms or optionally substituted phenyl radicals, or is a

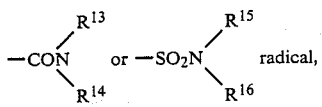

the radicals $R^{13}$ to $R^{16}$ representing hydrogen, alkyl having 1-6 carbon atoms or an optionally substituted phenyl radical, $R^1$, $R^2$, $R^3$, $R^4$, $R^5$ and $R^6$ represent hydrogen, an alkyl group having 1-6 carbon atoms which is optionally substituted by halogen, nitro, cyano, hydroxyl, alkoxy or alkylmercapto each having 1-3 carbon atoms, aryloxy, arylthio or an ester group having 1-3 carbon atoms in the alcohol moiety, or a phenyl radical, naphthyl radical or heterocyclic radical which is optionally substituted by halogen, nitro, alkyl or alkoxy or alkylmercapto each having up to 3 carbon atoms, hydroxyl, aryloxy, arylthio, cyano or an ester radical having 1-3 carbon atoms in the alcohol moiety, and $R^1$ and $R^2$, $R^3$ and $R^4$, $R^5$ and $R^6$ each can form, together with the carbon atom which connects them, a 3-7-membered ring which can optionally be substituted by optionally substituted alkyl radicals having 1-3 carbon atoms or optionally substituted aryl radicals, and furthermore $R^2$ with $R^3$ and/or $R^4$ with $R^5$ each can form, together with the carbon atom to which they are bonded, a 3-7-membered ring which is optionally substituted by optionally substituted alkyl radicals having 1-3 carbon atoms or optionally substituted aryl radicals, and n denotes 0 or 1, and when n denotes 1, $R^3$ and $R^4$ denote halogen, hydroxyl, alkoxy or alkylmercapto each having 1-3 carbon atoms, or a dialkylamino group having 1-3 carbon atoms in the alkyl radicals, comprising in a first reaction step reacting an enamine of the formula

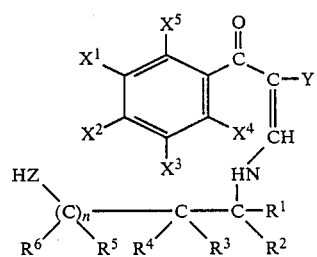

in which
  $X^3$ represents halogen, or a nitro group, and
  $X^4$ represents halogen, a nitro group, an alkoxy group having 1-3 carbon atoms in the alkyl moiety, an alkylmercapto or alkylsulphonyl group each having 1-3 carbon atoms in the alkyl radical, and an arylsulphonyl group, in an anhydrous, aprotic solvent with one equivalent of a base, at a temperature from 80° C. to 180° C., to give a 4-quinolone-3-carboxylic acid derivative of the formula

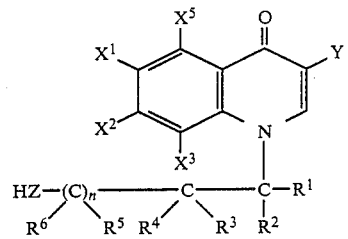

and, in a second reaction step, reacting that with another equivalent of a base, to give the 1,8-bridged 4-quinolone-3-carboxylic acid derivative of the formula (I) and optionally converting the group Y into a carboxyl group or salt thereof.

2. The process according to claim 1, wherein both steps with the base are effected simultaneously in a one-pot process without intermediate isolation of the compound II.

3. The process according to claim 1, in which
  $X^1$ is F,
  $X^2$ is F,
  $X^5$ is H,
  $R^1$ is $CH_3$,
  $R^2$ is $CH_3$,
  $R^3$ is H,
  $R^4$ is H,
  Y is COOH,
  n is O, and
  Z is oxygen.

4. The process according to claim 1, in which
  $X^1$ is F,
  $X^2$ is F,
  $X^5$ is H,
  $R^1$ is $CH_3$,
  $R^2$ is H,
  $R^3$ is $CH_3$,
  $R^4$ is H,
  Y is COOH,
  n is O, and
  Z is oxygen.

5. The process according to claim 1, in which
  $X^1$ is F,
  $X^2$ is F,
  $X^5$ is H,
  $R^1$ and $R^2$ together are $(CH_2)_5$,
  $R^3$ is H,
  $R^4$ is H,
  Y is COOH,
  n is O, and
  Z is oxygen.

6. The process according to claim 1, in which
  $X^1$ is F,
  $X^2$ is F,
  $X^5$ H,
  $R^1$ is $CH_2OH$,
  $R^2$ is H,
  $R^3$ is H,
  $R^4$ is H,
  Y is COOH, n is O, and
Z is oxygen.
7. The process according to claim 1, in which
$X^1$ is F,
$X^2$ is $CH_3$,
$X^5$ is H,
$R^1$ is H,
$R^2$ is H,
$R^3$ is H,
$R^4$ is H,
Y is COOH,
n is O, and
Z is oxygen.

* * * * *

UNITED STATES PATENT AND TRADEMARK OFFICE
CERTIFICATE OF CORRECTION

PATENT NO. : 4,859,773
DATED : August 22, 1989
INVENTOR(S) : Klaus Grohe, et al

It is certified that error appears in the above-identified patent and that said Letters Patent is hereby corrected as shown below:

| | |
|---|---|
| Abstract, line 8 | Delete "form" and substitute --from-- |
| Col. 3, line 44 | Delete "oof" and substitute --of-- |
| Col. 5, line 17 | Insert --R=$CH_3$, $C_2H_5$, $C_3H_{7-n}$-- |
| Col. 12, Table 2, Examples 41 and 44 | Move "-$(CH_2)_4$-" to span both columns "$R^2$" and "$R^3$" |
| Col. 13, Table 3, Example 63 | Delete entire line and substitute --Example 63, $X^1$ F, $X^2$ F, $X^5$ H, $R^1$ H, $R^2$ -$(CH_2)_4$-, $R^3$, $R^4$ H, $R^5$ H, $R^6$ H, Y COOH, Melting Point 274-6° (d)-- |
| Col. 15, line 44 | Correct spelling of --turkeys-- |
| Col. 20, line 63 | After "$X^5$" insert --is-- |

Signed and Sealed this

Twentieth Day of November, 1990

Attest:

HARRY F. MANBECK, JR.

*Attesting Officer*  *Commissioner of Patents and Trademarks*